United States Patent
Pleban

(10) Patent No.: US 8,830,470 B2
(45) Date of Patent: Sep. 9, 2014

(54) METHOD FOR MEASURING THE CONCENTRATION OF AT LEAST ONE GAS COMPONENT IN A MEASURING GAS

(75) Inventor: Kai-Uwe Pleban, Stutensee (DE)

(73) Assignee: Siemens Aktiengesellschaft, Munich (DE)

( * ) Notice: Subject to any disclaimer, the term of this patent is extended or adjusted under 35 U.S.C. 154(b) by 224 days.

(21) Appl. No.: 13/516,168

(22) PCT Filed: Dec. 8, 2010

(86) PCT No.: PCT/EP2010/069137
§ 371 (c)(1),
(2), (4) Date: Sep. 24, 2012

(87) PCT Pub. No.: WO2011/082925
PCT Pub. Date: Jul. 14, 2011

(65) Prior Publication Data
US 2013/0145813 A1    Jun. 13, 2013

(30) Foreign Application Priority Data

Dec. 15, 2009  (DE) .......................... 10 2009 058 394

(51) Int. Cl.
| | | |
|---|---|---|
| *G01N 21/00* | (2006.01) | |
| *G01N 21/35* | (2014.01) | |
| *G01N 21/25* | (2006.01) | |
| *G01N 21/39* | (2006.01) | |
| *G01N 21/27* | (2006.01) | |

(52) U.S. Cl.
CPC ............ *G01N 21/25* (2013.01); *G01N 21/3504* (2013.01); *G01N 21/39* (2013.01); *G01N 21/274* (2013.01)
USPC ....................................... 356/437

(58) Field of Classification Search
USPC ................................ 356/432–444
See application file for complete search history.

(56) References Cited

U.S. PATENT DOCUMENTS

| | | | | |
|---|---|---|---|---|
| 3,732,017 | A | * | 5/1973 | Wolber .......................... 356/436 |
| 3,788,742 | A | * | 1/1974 | Garbuny ....................... 356/5.03 |
| 3,812,330 | A | * | 5/1974 | Bowman et al. ................ 377/50 |
| 3,899,252 | A | * | 8/1975 | Dimeff ............................ 356/51 |
| 3,970,430 | A | * | 7/1976 | Reader et al. ................. 436/116 |
| 4,027,972 | A | * | 6/1977 | Davies ............................ 356/51 |
| 4,410,273 | A |   | 10/1983 | Mantz et al. |

(Continued)

FOREIGN PATENT DOCUMENTS

| | | |
|---|---|---|
| CN | 1177399 | 3/1998 |
| DE | 102 02 918 | 10/2003 |

(Continued)

*Primary Examiner* — Gregory J Toatley
*Assistant Examiner* — Jarreas C Underwood
(74) *Attorney, Agent, or Firm* — Cozen O'Connor

(57) ABSTRACT

A method for measuring a concentration of at least one gas component in a measurement gas, wherein light of a light source is guided along a light path through a measuring volume containing the measuring gas to a detector unit, and the concentration of the gas component is determined from the wavelength-dependent absorption of the light detected there. The light path is guided outside of the measuring volume through a substitute gas held in a closed volume. A substitute gas comprising a substitute gas component in a predetermined concentration is used, and the concentration of the substitute gas component is monitored based on the detected wavelength-dependent absorption, and if the decrease in the concentration exceeds a predetermined degree, then an error message is generated.

5 Claims, 1 Drawing Sheet

(56) References Cited

U.S. PATENT DOCUMENTS

| | | | |
|---|---|---|---|
| 4,937,448 A * | 6/1990 | Mantz et al. | 250/343 |
| 5,387,971 A * | 2/1995 | Koashi et al. | 356/246 |
| 5,747,809 A | 5/1998 | Eckstrom | |
| 5,964,712 A * | 10/1999 | Kubo et al. | 600/529 |
| 6,274,870 B1 | 8/2001 | Kubo et al. | |
| 6,444,985 B1 * | 9/2002 | Mori et al. | 250/339.13 |
| 7,324,204 B2 | 1/2008 | Kluczynski | |
| 7,864,323 B2 * | 1/2011 | Kluczynski et al. | 356/439 |
| 8,089,046 B2 * | 1/2012 | Davis et al. | 250/356.1 |

FOREIGN PATENT DOCUMENTS

| | | |
|---|---|---|
| DE | 103 45 507 | 5/2005 |
| EP | 1 693 665 | 8/2006 |
| EP | 2 000 792 | 12/2008 |
| WO | WO 97/47957 | 12/1997 |

* cited by examiner

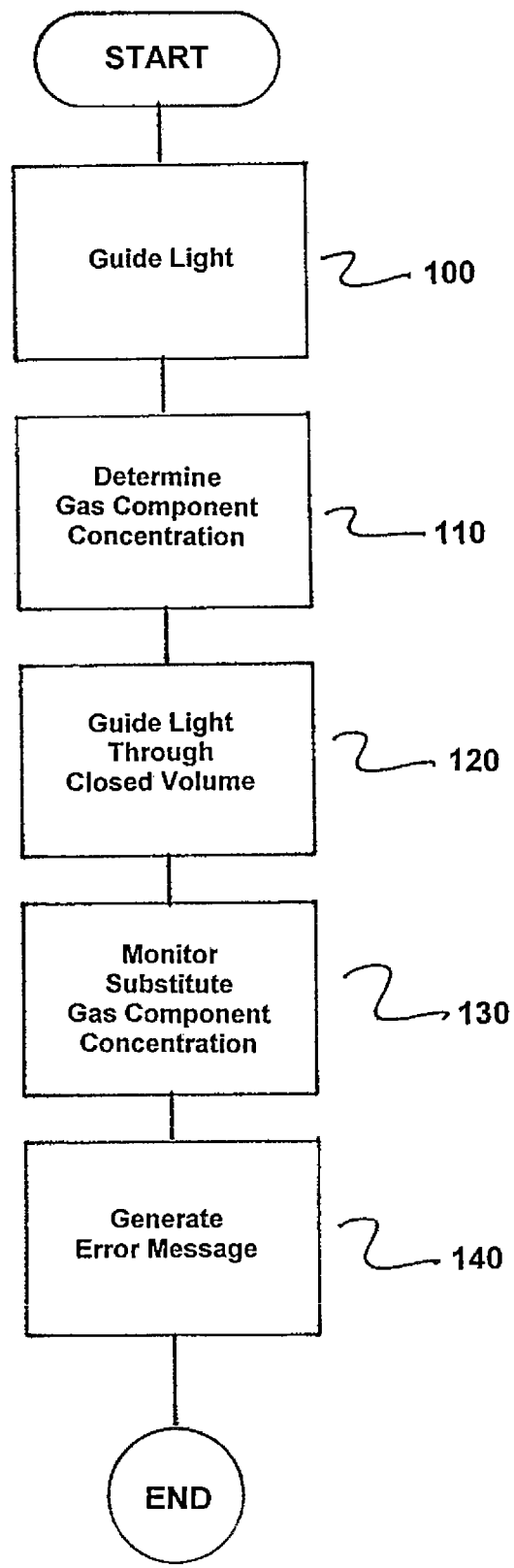

METHOD FOR MEASURING THE CONCENTRATION OF AT LEAST ONE GAS COMPONENT IN A MEASURING GAS

CROSS-REFERENCE TO RELATED APPLICATIONS

This is a U.S. national stage of application No. PCT/EP2010/069137 filed 8 Dec. 2010. Priority is claimed on German Application No. 10 2009 058 394.7 filed 15 Dec. 2009, the content of which is incorporated herein by reference in its entirety.

BACKGROUND OF THE INVENTION

1. Field of the Invention

The invention relates to a method for measuring the concentration of at least one gas component in a measurement gas.

2. Description of the Related Art

In a conventional method described in EP 1 693 665 A1, a measurement gas with a gas component to be determined therein is guided through a measurement volume comprising a measurement cuvette or, for in-situ measurements, comprising a tube or another system part conveying gas. The measurement volume has two windows with an optical measurement path of predetermined length lying between them. A wavelength-tunable light source, for example, a diode laser, generates a light beam, having a wavelength that is tuned to an absorption line of the gas component to be determined and which is directed through the measurement volume onto a detector. The signal generated by the detector is dependent on the light absorption in the measurement volume. As a result, the concentration of the gas component can be calculated from the signal while taking into account the specific absorption coefficient of the gas component and the known measurement path length.

The lower the concentration of the gas component to be measured is, the greater is the effect of perturbing absorptions that are due to components of the ambient air in the regions of the light path outside the measurement volume, i.e., between the light source and the measurement volume as well as between the measurement volume and the detector. It is therefore known to flush these regions with a gas that exhibits no absorption in the wavelength range of the absorption line of the gas component to be measured. A flushing gas suitable for many cases is, for example, nitrogen. Continuous flushing with fresh flushing gas, however, is associated with relatively high operating costs.

From the aforementioned EP 1 693 665 A1 publication, it is furthermore known to separately detect perturbing gas components, which as constituents of the ambient air may possibly enter the flushing gas path through a leak, and thereby correct the measurement result. To this end, the light from the light source is split into two sub-beams, one of which is directed through the measurement gas volume onto the aforementioned detector and the other of which is directed onto a second detector through a cuvette, through which the flushing gas flows.

From U.S. Pat. No. 5,747,809, it is known to guide the flushing gas in a circuit through a filter comprising an absorber substance, in order to remove perturbing gas components, which as constituents of the ambient air may possibly enter the flushing gas circuit through a leak. Since, depending on the effectiveness of the filter, the perturbing gas components may possibly be removed only incompletely, here again perturbing gas components entering the flushing gas are separately detected in order thereby to correct the measurement result. To this end, similarly as in the case of the EP 1 693 665 A1 publication, the light from the light source is split into two sub-beams, one of which is directed through the measurement gas volume onto the detector and the other of which is directed onto a second detector through a cuvette, through which the flushing gas flows.

From EP 2 000 792 A1, it is known to arrange a reference volume in series with the measurement volume in the light path. The reference volume contains the measurement gas component, for example oxygen, with a particular isotope, for example $^{18}O_2$, in a particular $_{16}O:^{18}O_2$ abundance ratio that is higher than the known natural abundance ratio of these isotopes in the gas component in the measurement volume. The absorption lines of the two isotopes $^{16}O_2$ and $^{18}O_2$ are scanned with the light. The concentration of the gas component in the measurement volume is calculated from the ratio of the detector signals at the peaks of the absorption lines based on Lambert's law and while taking into account the known isotope abundance ratios. For wavelength stabilization of the tunable light source, the wavelength may be locked to the absorption line of the $^{18}O_2$ isotope. The problematic perturbing absorptions due to components of the ambient air in the regions of the light path outside the measurement volume and reference volume is not part of the subject-matter of EP 2 000 792 A1 and is not mentioned there.

SUMMARY OF THE INVENTION

It is an object of the invention to ensure, in a simple way and with little outlay, that a measurement result of at least one gas component in a measurement gas that is delivered is not influenced by perturbing components of the ambient air in the regions of the light path outside the measurement volume which are filled with a substitute gas.

This and other objects and advantages are achieved in accordance with the invention by providing a method for measuring the concentration of at least one gas component in a measurement gas in which the light from a light source is guided along a light path through a measurement volume containing the measurement gas to a detector unit, and the concentration of the gas component is determined from the wavelength-dependent absorption of light which is detected there. In addition, the region of the light path outside the measurement volume is guided through a closed volume which holds a substitute gas without constant gas supply and discharge. Further, a substitute gas is used with a substitute gas component in a predetermined concentration, where the substitute gas component is not present in the atmosphere and the measurement gas, or is present in a concentration substantially lower than the predetermined concentration, or in a known ratio to the gas component to be measured. Moreover, the concentration of the substitute gas component is monitored with the aid of the detected wavelength-dependent absorption of the light, and an error message is generated in the event of a concentration decrease exceeding a predetermined amount.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The FIGURE is a flowchart of the method in accordance with an embodiment of the invention.

DETAILED DESCRIPTION OF THE PREFERRED EMBODIMENTS

The FIGURE a flow chart illustrating the method for measuring the concentration of at least one gas component in a measurement gas. The method comprises guiding light from a light source along a light path through a measurement volume containing the measurement gas to a detector unit; as indicated in step 100. The concentration of the gas component from a wavelength-dependent absorption of light detected in the measurement volume is determined, as indicated in step 110.

A region of the light path is guided outside the measurement volume through a closed volume which holds a substitute gas without constant gas supply and discharge, as indicated in step 120. Here, the substitute gas is used with a substitute gas component in a predetermined concentration, where the substitute gas component is either not present in an atmosphere and the measurement gas, present in the atmosphere and the measurement gas in a concentration substantially lower than the predetermined concentration, or present in the measurement gas at a known ratio to the gas component to be measured.

The concentration of the substitute gas component is then monitored, aided by the detected wavelength dependent absorption of the light, as indicated in step 130. An error message is generated in an event of a concentration decrease of the substitute gas component exceeding a predetermined amount, as indicated in step 140.

The substitute gas is held in the closed volume without constant gas supply and discharge. As a result, the operating costs associated with continuous flushing with fresh flushing gas are avoided. On the other hand, however, the substitute gas filling is only as good as the leak tightness of the closed volume. Detection of perturbing gas components entering the closed volume in the event of leakage would, as described in the aforementioned EP 1 693 665 A1 and U.S. Pat. No. 5,747,809 publications, require splitting of the light from the light source into two sub-beams, a cuvette through which the flushing gas flows and a second detector. The method of the invention makes use of the fact that substitute gas escapes from the volume to the same extent as ambient air enters the closed volume, and therefore proposes to monitor a predetermined, i.e., a known, concentration of a selected substitute gas component in the closed volume. In the event of a concentration decrease exceeding a predetermined amount, an error message is generated which indicates that the measurement result for the concentration of the gas component in the measurement gas is perturbed, or at least is not reliable.

When a wavelength-tunable light source (for example, a laser spectrometer) is used, the determination of the concentration of the gas component and the monitoring of the concentration of the substitute gas component are performed with the same detector at different wavelengths. In other optical methods (for example, NDIR gas analysis), for example, two detectors placed in succession may, for example, be used for the gas component and the substitute gas component, or when using a single detector different spectral filters are moved through the light path periodically one after the other.

The selected substitute gas component may be one or more components of the substitute gas or the substitute gas itself, although the substitute gas does not contain the gas component to be measured so as not to compromise the measurement. There is an exception for the case in which the substitute gas component is present in the measurement volume in a known ratio to the gas component of the measured. This may, in particular, apply for isotopes.

Thus, for measurement of the oxygen concentration in the measurement gas, the concentration of the oxygen isotope $^{16}O_2$ is determined and the oxygen isotope $^{18}O_2$ is used as the substitute gas component. The oxygen concentration to be determined is then calculated, or calibrated for set-up, from the measured concentration of the oxygen isotope $^{16}O_2$ and the known natural abundance ratio of the isotopes $^{16}O_2$ and $^{18}O_2$. The concentration to be monitored of the substitute gas component, here the isotope $_{18}O_2$, is corrected by the $^{18}O_2$ concentration in the measurement gas calculated from the measured $^{16}O_2$ concentration while taking into account the natural isotope abundance ratio.

Moreover, a substitute gas component is used that does not occur in the atmosphere and the measurement gas, or which occurs only in a substantially lower concentration than the predetermined concentration in the closed volume. In this context, a substantially lower concentration is intended to mean one that is negligible in comparison with the concentration decrease of the substitute gas component in the closed volume that leads to the error message.

An absorption line of the gas component to be measured in the measurement gas and an absorption line of the substitute component are respectively scanned with the light generated by the wavelength-tunable light source. With the aid of the detected wavelength-dependent absorption of the light, the concentration of the substitute gas component is monitored and, in the event of a concentration decrease exceeding a predetermined amount, the error message is generated. The measurement of the gas component of interest and of the substitute gas component may be performed in parallel or in time division multiplex, but with only one measurement channel being used, i.e., one light beam and one detector.

Furthermore, the substitute gas component to be monitored may advantageously be used for wavelength stabilization of the tunable light source, by locking the wavelength to the absorption line of the substitute gas component, as is known from EP 2 000 792 A1.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those method steps which perform substantially the same function in substantially the same way to achieve the same results are within the scope of the invention. Moreover, it should be recognized that method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method for measuring a concentration of at least one gas component in a measurement gas, comprising:
    guiding light from a light source along a light path through a measurement volume containing the measurement gas to a detector unit;
    determining the concentration of the gas component from a detected gas component-specific wavelength-dependent absorption of the light;
    guiding a region of the light path outside the measurement volume through a closed volume which holds a substitute gas without constant gas supply and discharge, the substitute gas being used with a substitute gas component in a predetermined concentration, the substitute gas component being one of not present in an atmosphere and the measurement gas, present in the atmosphere and the measurement gas in a concentration of at least half the predetermined concentration, and present in the measurement gas at a known ratio to the gas component to be measured;
    monitoring the concentration of the substitute gas component using a detected substitute gas component-specific wavelength-dependent absorption of the light; and
    generating an error message in an event of a concentration decrease of the substitute gas component exceeding a predetermined amount.

2. The method as claimed in claim 1, wherein, when a wavelength-tunable light source is used, the wavelength is locked to an absorption line of the substitute gas component to stabilize a wavelength of the wavelength-tunable light source.

3. The method as claimed in claim 1, wherein the substitute gas component comprises an isotope of the gas component to be measured, a natural abundance of which is at least one of low and known.

4. The method as claimed in claim 2, wherein the substitute gas component comprises an isotope of the gas component to be measured, a natural abundance of which is at least one of low and known.

5. The method as claimed in claim 3, further comprising:
    determining a concentration of an oxygen isotope $^{16}O_2$, the substitute gas component comprising an oxygen isotope $^{18}O_2$;
    calculating the oxygen concentration to be measured from the determined concentration of the oxygen isotope $^{16}O_2$ and a natural abundance ratio of the isotopes $^{16}O_2$ and $^{18}O_2$ to measure the oxygen concentration in the measurement gas; and
    correcting the concentration of the substitute gas component to be monitored by the calculated concentration of the isotope $^{18}O_2$ in the measurement gas.

* * * * *